United States Patent [19]
Goldenberg

[11] Patent Number: 5,989,243
[45] Date of Patent: *Nov. 23, 1999

[54] EXCIMER LASER ANGIOPLASTY SYSTEM

[75] Inventor: Tsvi Goldenberg, Irvine, Calif.

[73] Assignee: Advanced Interventional Systems, Inc., Irvine, Calif.

[ * ] Notice: This patent is subject to a terminal disclaimer.

[21] Appl. No.: 07/990,514

[22] Filed: Dec. 15, 1992

Related U.S. Application Data

[63] Continuation-in-part of application No. 07/593,485, Oct. 3, 1990, Pat. No. 5,188,632, which is a continuation of application No. 07/218,907, Jul. 14, 1988, abandoned, which is a continuation-in-part of application No. 07/051,382, May 19, 1987, Pat. No. 4,830,460, application No. 06/860,241, May 6, 1986, Pat. No. 4,799,754, application No. 06/779,844, Sep. 25, 1985, Pat. No. 4,732,488, and application No. 06/679,538, Dec. 7, 1984, Pat. No. 4,641,912.

[51] Int. Cl.$^6$ ...................................................... A61N 5/06
[52] U.S. Cl. ........................ 606/7; 606/3; 606/1; 606/15
[58] Field of Search ............................ 606/3–5, 7, 10–18

[56] References Cited

U.S. PATENT DOCUMENTS

| | | |
|---|---|---|
| Re. 31,289 | 6/1983 | Moore et al. . |
| Re. 31,290 | 6/1983 | Moore et al. . |
| 3,327,712 | 6/1967 | Kaufman et al. . |
| 3,434,775 | 3/1969 | Gosselin . |

(List continued on next page.)

FOREIGN PATENT DOCUMENTS

| | | |
|---|---|---|
| 0153847 | 9/1985 | European Pat. Off. . |
| 25 17 019 | 10/1976 | Germany . |
| 59-111125 | 6/1984 | Japan . |
| 59-228602 | 12/1984 | Japan . |
| 214712 | 4/1924 | United Kingdom . |
| 1042281 | 9/1966 | United Kingdom . |
| 2 095 422 | 9/1982 | United Kingdom . |
| WO83/03144 | 9/1983 | WIPO . |
| WO85/02532 | 6/1985 | WIPO . |
| WO86/03598 | 6/1986 | WIPO . |

OTHER PUBLICATIONS

Taylor, R.S., Microsecond Duration Optical Pulses From a UV–preionized XeCI Laser, Appl. Phys.Lett., vol. 47, No. 2, Jul. 15, 1985, pp. 81–83.

Grundfest, W.S., Pulsed Ultraviolet Lasers and the Potential for Safe Laser Angioplasty, The American Journal of Surgery, vol. 150, Aug. 1985, pp. 220–226.

(List continued on next page.)

*Primary Examiner*—David M. Shay
*Attorney, Agent, or Firm*—Pillsbury Madison & Sutro, LLP

[57] ABSTRACT

A fiber-optic waveguide, used for ablating lesions in blood vessels, is mounted within and guided by a catheter having multiple lumens extending therethrough and parallel to each other. The waveguide fits within at least one lumen and a guidewire, previously inserted in a blood vessel, extends through another lumen. The distal end of the waveguide can have a short section of larger diameter fiber fused to it to cause a laser beam transmitted through the fiber to expand as it emerges from the waveguide to provide a larger ablation area. The waveguide may also be connected to an energy source by means of an energy coupler.

9 Claims, 4 Drawing Sheets

U.S. PATENT DOCUMENTS

| | | |
|---|---|---|
| 3,556,085 | 1/1971 | Takahashi . |
| 3,756,690 | 9/1973 | Borrelli et al. . |
| 3,844,752 | 10/1974 | Kaiser . |
| 3,858,577 | 1/1975 | Bass et al. . |
| 3,920,980 | 11/1975 | Nath . |
| 3,922,063 | 11/1975 | Marrone . |
| 3,950,187 | 4/1976 | Kirkpatrick . |
| 3,966,300 | 6/1976 | Bernsee . |
| 3,969,016 | 7/1976 | Kaiser et al. . |
| 3,987,781 | 10/1976 | Nozik et al. . |
| 4,009,382 | 2/1977 | Nath . |
| 4,011,403 | 3/1977 | Epstein et al. . |
| 4,045,119 | 8/1977 | Eastgate . |
| 4,082,958 | 4/1978 | Kirkpatrick . |
| 4,092,515 | 5/1978 | Joslin et al. . |
| 4,151,080 | 4/1979 | Zuckerman et al. . |
| 4,173,392 | 11/1979 | Ekinaka et al. . |
| 4,173,393 | 11/1979 | Maurer . |
| 4,190,759 | 2/1980 | Hongo et al. . |
| 4,199,218 | 4/1980 | Steinhage et al. . |
| 4,207,874 | 6/1980 | Choy . |
| 4,221,825 | 9/1980 | Guerder et al. ............................. 427/34 |
| 4,229,232 | 10/1980 | Kirkpatrick . |
| 4,248,213 | 2/1981 | Landre . |
| 4,266,548 | 5/1981 | Davi . |
| 4,270,845 | 6/1981 | Takizawa et al. . |
| 4,272,156 | 6/1981 | Ishibashi et al. . |
| 4,273,109 | 6/1981 | Enderby . |
| 4,286,232 | 8/1981 | Puech et al. . |
| 4,305,640 | 12/1981 | Cullis et al. . |
| 4,331,132 | 5/1982 | Mukamu . |
| 4,345,212 | 8/1982 | Seppala et al. . |
| 4,361,139 | 11/1982 | Takagi . |
| 4,367,729 | 1/1983 | Ogiu . |
| 4,370,175 | 1/1983 | Levatter . |
| 4,388,924 | 6/1983 | Weissman et al. . |
| 4,392,485 | 7/1983 | Hiltebrandt . |
| 4,392,715 | 7/1983 | Bonewitz et al. . |
| 4,398,790 | 8/1983 | Righini et al. . |
| 4,418,688 | 12/1983 | Loeb . |
| 4,418,689 | 12/1983 | Kanazawa . |
| 4,419,987 | 12/1983 | Ogiu . |
| 4,445,754 | 5/1984 | Beales et al. . |
| 4,445,892 | 5/1984 | Hussein et al. . |
| 4,448,547 | 5/1984 | Wickersheim . |
| 4,469,098 | 9/1984 | Davi . |
| 4,490,020 | 12/1984 | Sakaguchi et al. . |
| 4,504,114 | 3/1985 | Arrington . |
| 4,511,209 | 4/1985 | Skutnik . |
| 4,521,070 | 6/1985 | Sottini et al. . |
| 4,526,170 | 7/1985 | Tanner . |
| 4,560,286 | 12/1985 | Wickersheim . |
| 4,565,197 | 1/1986 | Daly . |
| 4,569,335 | 2/1986 | Tsuno . |
| 4,576,435 | 3/1986 | Nishioka . |
| 4,583,539 | 4/1986 | Karlin et al. . |
| 4,627,436 | 12/1986 | Leckrone . |
| 4,641,650 | 2/1987 | Mok . |
| 4,641,912 | 2/1987 | Goldenberg . |
| 4,646,737 | 3/1987 | Hussein et al. . |
| 4,652,083 | 3/1987 | Laakmann . |
| 4,657,014 | 4/1987 | Edelman et al. . |
| 4,665,913 | 5/1987 | L'Esperance ............................... 606/3 |
| 4,672,961 | 6/1987 | Davies . |
| 4,677,636 | 6/1987 | Laudenslager et al. . |
| 4,681,104 | 7/1987 | Edelman . |
| 4,681,396 | 7/1987 | Jones . |
| 4,682,594 | 7/1987 | Mok . |
| 4,686,979 | 8/1987 | Gruen et al. . |
| 4,690,500 | 9/1987 | Hayami et al. . |
| 4,729,621 | 3/1988 | Edelman . |
| 4,732,448 | 3/1988 | Goldenberg . |
| 4,747,405 | 5/1988 | Leckrone . |
| 4,784,132 | 11/1988 | Fox et al. . |
| 4,800,876 | 1/1989 | Fox et al. . |
| 4,819,632 | 4/1989 | Davies . |
| 4,830,460 | 5/1989 | Goldenberg . |
| 4,832,023 | 5/1989 | Murphy-Chutorian et al. . |
| 4,848,336 | 7/1989 | Fox et al. . |
| 4,850,351 | 7/1989 | Herman et al. . |

OTHER PUBLICATIONS

Laudenslager, J.B., "Effect of 308–nm XeCI Laser Pulse Duration of Fiberoptic Transmission and Biologic Tissue Ablation" Conference on Lasers and Electro–Optics, Jun. 9–13, 1986, San Francisco, California.

Abela, G.S., Lasers in Cardiovascular Medicine and Surgery: Fundamentals and Techniques, Kluwer Academic Publishers, 1990, pp. 203–207.

Isner, J.M., Cardiovascular Laser Therapy, Raven Press, 1989, pp. 17–37.

White, R.A., "Catheters for Laser Angioplasty—Design Considerations", Lasers in Cardiovascular Disease: Clinical Applications, Alternative Angioplasty Devices, and Guidance Systems, Year Book Medical Publishers, 1989, pp. 49–71.

P. Kaiser et al, B.S.T.J. Brief: A New Optical Fiber, The Bell System Technical Journal, vol. 52, No. 2, Feb. 1973, pp. 265–269.

P. Kaiser et al, Spectral Losses of Unclad Vitreous Silica and Soda–Lime–Silicate Fibers, The Journal of Optical Society of America, vol. 63, No. 9, Sep. 1973, pp. 1141–1148.

P. Kaiser et al, Low–Loss Single–Material Fibers Made From Pure Fused Silica, The Bell System Technical Journal, vol. 53, No. 6, Jul.–Aug. 1974, pp. 1021–1039.

P. Kaiser, Drawing–Induced Coloration in Vitreous Silica Fibers, Journal of the Optical Society of America, vol. 64, No. 4, Apr. 1974, pp. 475–481.

H. Fujii et al, Fibre Bundle Scanner For Laser Photocoagulation Treatment, Optics and Laser Technology, Feb. 1982, pp. 39–40.

S.W. Allison et al, Use of Fiber Optics and Laser–Induced Fluorescence for Remote Measurements of $UF_6$ In Strong Rotation, Los Alamos National Laboratory, Jun. 1983, pp. 1–37.

Y. Itoh et al, High–Power KrF Laser Transmission Through Optical Fibers and Its Application to the Triggering of Gas Switches, Journal of Applied Physics, vol. 54, No. 6, Jun. 1983, pp. 2956–2961.

IBM's Heatless Laser Etching: A Hot IC and Medical Prospect, News Spectra, Jul. 1983, 1 page.

S. Trokel et al, Excimer Laser Surgery of the Cornea, American Journal of Ophthalmology, vol. 96, No. 6, Dec. 1983, pp. 710–715.

J.H. Stathis et al, Photoinduced Paramagnetic Defects in Amorphous Silicon Dioxide, The American Physical Society, vol. 29, No. 12, Jun. 15, 1984, pp. 7079–7081.

R. Linsker et al, Far–Ultraviolet Laser Ablation of Atherosclerotic Lesions, Lasers In Surgery and Medicine, Jul. 25, 1984, pp. 201–206.

J. Parrish et al, Laser Photomedicine, IEEE Journal of Quantum Electronics, vol. QE–20, No. 12, Dec. 1984, pp. 1386–1396.

D. Dorion, Laser Angioplasty, Tuesday Morning, TUA, Jun. 10, 1986, pp. 60–63.

T. Goldenberg et al, Design Criteria for In-Vivo Laser Angioplasty, Optical Fibers in Medicine II, SPIE vol. 713, 1986, pp. 53–56.

Mehta et al, Excimer Laser Coronary Angioplasty, CARDIO, Nov. 1991.

A. Coulter, AIS Excimer Angioplasty Device Approaches Approval After Tortuous Development Route, Journal of Clinical Laser Medicine & Surgery, vol. 9, No. 6, Dec. 1991, pp. 405–407.

J. Forrester et al, Coronary Excimer Laser Angioplasty, The Journal of Invasive Cardiology, vol. 4, No. 2, Mar. 1992, pp. 75–82.

J. Margolis et al, Excimer Laser Coronary Angioplasty, The American Journal of Cardiology, vol. 69, May 7, 1992, pp. 3F–11F.

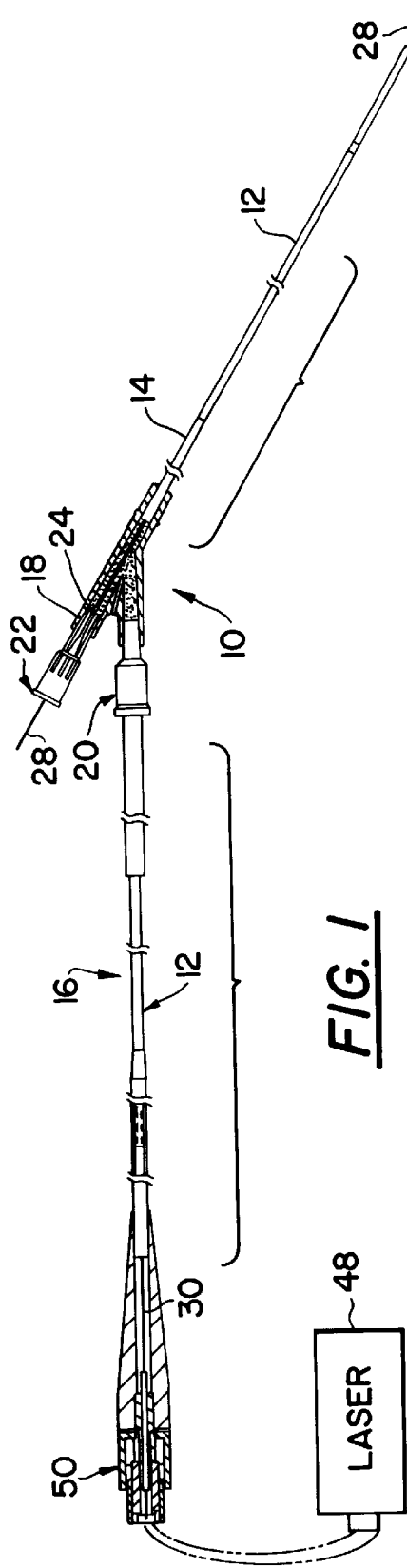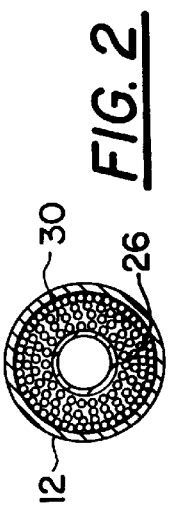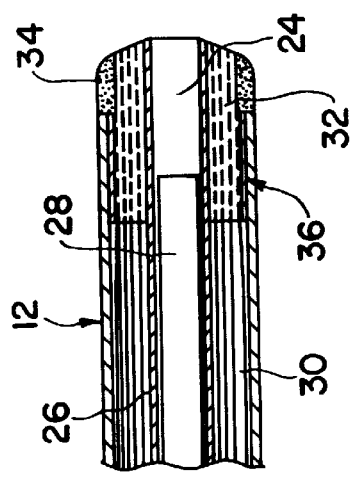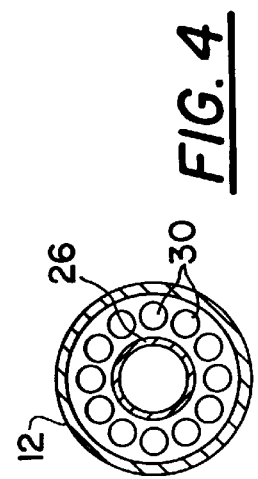

EXCIMER LASER ANGIOPLASTY SYSTEM

CROSS-REFERENCE TO RELATED APPLICATIONS

This is a continuation-in-part of application Ser. No. 593,485, filed Oct. 3, 1990, now U.S. Pat. No. 5,188,632, which is a continuation of Ser. No. 218,907, filed Jul. 14, 1988, abandoned. This latter application is itself a continuation-in-part of the following series of successive continuation-in-part applications: U.S. Ser. No. 051,382 filed May 19, 1987 (now U.S. Pat. No. 4,830,460), U.S. Ser. No. 860,241 filed May 6, 1986 (now U.S. Pat. No. 4,799,754), U.S. Ser. No. 779,844 filed Sep. 25, 1985 (now U.S. Pat. No. 4,732,488), and U.S. Ser. No. 679,538 filed Dec. 7, 1984 (now U.S. Pat. No. 4,641,912), the disclosures of which are herein incorporated by reference thereto.

BACKGROUND OF THE INVENTION

The present invention is directed to a system for delivering high energy laser light by means of an optical waveguide, and in one particular application is concerned with laser angioplasty and a means for guiding such a system.

The use of laser energy to ablate atherosclerotic plaque that forms an obstruction in a blood vessel is a viable alternative to coronary bypass surgery. This procedure, known as angioplasty, essentially involves insertion of a fiberoptic waveguide catheter into the blood vessel, and conduction of laser energy through the catheter's waveguide to direct it at the plaque once the distal end of the catheter is positioned adjacent the obstruction.

Most of the early experimentation and testing that was done in this area utilized continuous wave laser energy, such as that produced by Argon Ion, Nd:YAG or Carbon Dioxide lasers. The light produced by this type of laser is at a relatively low energy level, and it can be readily conducted through an optical fiber. Ablation of the obstruction is achieved with these types of lasers by heating the plaque with constant laser power over a period of time until the temperature is great enough to destroy it.

While the use of continuous wave laser energy has been found to be sufficient to ablate an obstruction, it is not without its drawbacks. Most significantly, the destruction of the lesion is uncontrolled and is accompanied by thermal injury to the vessel walls immediately adjacent the obstruction. In an effort to avoid such thermal injury and to provide better control of the tissue removal, the use of a different, higher level form of laser energy having a wavelength in the ultra-violet range (40–400 nanometers) has been suggested. See, for example, International Patent Application PCT/US84/02000, published Jun. 20, 1985. One example of a laser for producing this higher level energy is known as the Excimer laser, which employs a laser medium such as argon-fluoride having a wavelength of 193 nanometers, krypton-chloride (222 nm), krypton-fluoride (248 nm), xenon-chloride (308 nm) or xenon-fluoride (351 nm). The light produced by this type of laser appears in short bursts or pulses that typically last in the range of tens of nanoseconds and have a high peak energy level, for example as much as 200 mJ. Although the destruction mechanism involving this form of energy is not completely understood, it has been observed that each single pulse of the Excimer laser produces an incision which destroys the target tissue without significant accompanying thermal injury to the surrounding area. This result, which is referred to as "photoablation", has been theorized to be due to either or both of two phenomena. The delivery of the short duration, high energy pulses may vaporize the material so rapidly that heat transfer to the non-irradiated adjacent tissue is minimal. Alternatively, or in addition, ultraviolet photons absorbed in the organic material might disrupt molecular bonds to remove tissue by photochemical rather than thermal mechanisms.

While the high peak energy provided by Excimer and other pulsed lasers has been shown to provide improved results with regard to the ablation of atherosclerotic plaque, the high energy and power density also presents a serious practical problem. Typically, to couple a large diameter laser beam into a smaller diameter fiber or bundle of fibers, the input ends of the fibers are ground and polished to an optical grade flat surface. Residual impurities from the polishing compound and gross scratches on the surface absorb the laser energy. These imperfections result in localized expansion at the surface of the fiber when the laser energy is absorbed. The high energy and high power Excimer laser pulses contribute to high shear stresses which destroy the integrity of the fiber surface. Continued application of the laser energy causes a deep crater to be formed inside the fiber. Thus, it is not possible to deliver a laser pulse having sufficient energy to ablate tissue in vivo using a conventional system designed for continuous wave laser energy.

This problem associated with the delivery of high-energy, high-power laser pulses is particularly exacerbated in the field of coronary angioplasty because of the small diameter optical fibers that must be used. For example, a coronary artery that is appropriate for laser angioplasty typically has an internal diameter of about three millimeters or less. Accordingly, the total external diameter of a coronary angioplasty catheter system is typically less than two and one-half millimeters. If this catheter system is composed of multiple optical fibers arranged adjacent one another, it will be appreciated that each individual fiber must be quite small in cross-sectional area.

A critical parameter with regard to the destruction of an optical fiber is the density of the energy and power that is presented to the end of the fiber. In order to successfully deliver the laser energy, the energy and power density must be maintained below the destruction threshold of the fiber. Thus, it will be appreciated that fibers having a small cross-sectional area, such as those used in angioplasty, can conduct only a limited amount of energy if the density level is maintained below the threshold value. This limited amount of energy may not be sufficient to efficiently ablate the obstructing tissue or plaque without thermal damage.

Even if the energy density is quite high, the small beam that results from a small diameter fiber may not have a sufficiently large target area that effective ablation of the lesion results. Only a small fragment of the lesion might be ablated, and thus not provide adequate relief from the blockage.

A further problem with the use of a fiberoptic waveguide catheter to direct laser energy for purposes of ablating atherosclerotic plaque is that of perforation of the blood vessel. Such perforations can be caused by the catheter itself contacting and mechanically perforating the vessel. Such perforations can also be caused by the laser beam, particularly if the catheter is not aligned properly within the blood vessel. The perforation problems are related to the intrinsic stiffness of the glass fibers of the waveguide catheter and poor control of laser energy at the distal end of the fibers, regardless of laser source or wavelength.

Also related to the stiffness of the glass fibers is the ability to control the position of the laser-conducting fibers radially within the blood vessels. The conventional systems that employ a fiberoptic waveguide catheter within a blood vessel do not provide means for controlling radial movement within the blood vessel.

One known attempt at developing an angioplasty catheter is disclosed in U.S. Pat. No. 4,747,405. The known catheter includes a center guidewire lumen, a guidewire therein, and a single optical fiber disposed at a side of the catheter for emitting laser energy. The catheter also has a blunt leading end that does not facilitate progress through a blood vessel. A particular problem that potentially results from the use of a catheter with a single optical fiber is that large segments of the ablated lesion may become loose in the blood stream and could possibly cause an emboli. As a result, the known catheter includes a dedicated channel to remove the loosened debris.

OBJECTS AND BRIEF STATEMENT OF THE INVENTION

Accordingly, it is a general object of the invention to provide a novel system for delivering high energy pulsed laser light using an optical waveguide.

It is a more specific object of the invention to provide such a delivery system that is particularly well suited to deliver pulsed ultraviolet laser energy in vivo for the ablation of atherosclerotic plaque. In this regard, it is a particular object of the present invention to provide a highly efficient catheter for use in such a delivery system.

It is yet another object of the present invention to provide such a delivery system that is adapted to minimize the likelihood of perforating or otherwise damaging a blood vessel in which the system is being used.

It is a further object of the present invention to provide such a system that includes a guide for facilitating the maneuvering of the optical waveguides through the blood vessel in which the system is being used.

It is another object of the present invention to provide a device for controlling the radial position of the optical waveguide catheter within the blood vessel in which the system is being used.

Another object of the present invention is to provide an angioplasty catheter that is able to remove lesions in small pieces so as to minimize the risk of emboli.

Briefly, one aspect of a delivery system embodying the present invention relates to a guidance system that facilitates guiding an optical fiber catheter system through a blood vessel. In a preferred form, the guidance system comprises a guidewire that is inserted into the blood vessel prior to the insertion of the optical waveguide, and a catheter having lumens extending therethrough to accommodate the guidewire and the waveguide. The distal ends of the optical fibers are bonded within one of the catheter lumens. The wire is first inserted into the blood vessel to a location beyond the lesion. The catheter is then advanced along the wire until the ends of the optical fibers are positioned adjacent a lesion to be ablated by pulsed ultraviolet laser energy conducted through the optical fiber system. The wire functions as a guide track to keep the ablation site co-linear with the blood vessel as the catheter is advanced during the ablation process.

Radial control of the optical fiber within the blood vessel may be obtained by locating the fiber lumen eccentrically within the catheter. By rotating the catheter, the optical fiber portion of the catheter can be moved to different radial positions within the blood vessel.

In another preferred embodiment of the present invention, a multilumen, multifiber catheter is employed to deliver the laser energy to the desired site within the blood vessel. The catheter includes a central, axially disposed lumen which accommodates the guidewire. One or more lumens located radially outwardly and circumferentially around this central lumen house multiple fibers which are used to deliver the laser energy. With this arrangement, an output beam having a relatively large effective diameter is produced, to ablate a significant portion of the obstruction.

Further along these lines, the distal ends of the fibers can be provided with a larger diameter to cause the laser beam to expand as it exits the catheter, and thereby produce a larger area of coverage from fewer fibers.

Further features of the present invention and preferred modes for implementing them will become apparent from the following detailed description of preferred embodiments of the invention illustrated in the accompanying drawings.

BRIEF DESCRIPTION OF THE DRAWINGS

FIG. 1 is a side view, partly in cross-section, of a catheter delivery system for high-energy Excimer laser light;

FIG. 2 is a cross-sectional distal end view of one embodiment of the catheter;

FIG. 3 is a more detailed cross-sectional side view of the distal end of the catheter;

FIG. 4 is a cross-sectional distal end view of another embodiment of the catheter;

DESCRIPTION OF THE ILLUSTRATED EMBODIMENTS

Figure 6:
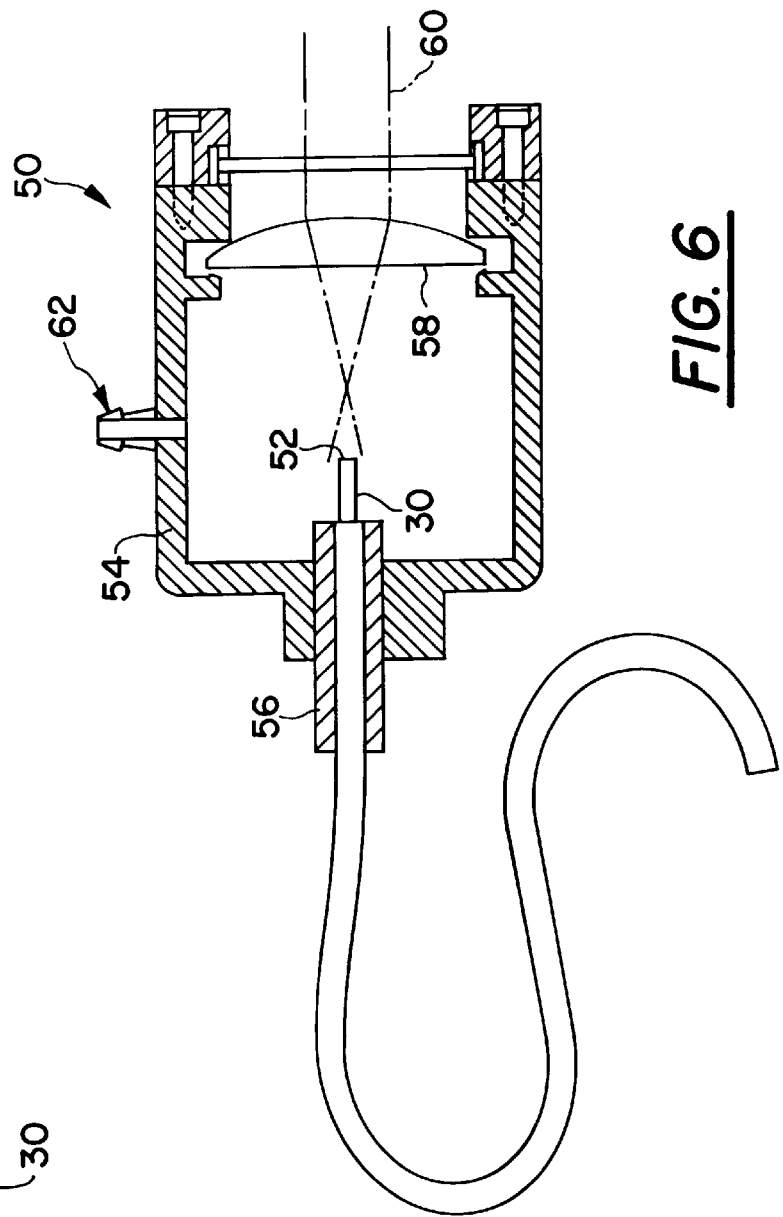
FIG. 6 is an enlarged view of the proximal portion of the catheter, illustrating the coupling mechanism.

In the following specification, a laser delivery system is described with particular reference to the use of a high-energy pulsed ultraviolet laser, such as an Excimer laser, in an angioplasty system, to facilitate an understanding of the invention and its uses.

Referring now to FIG. 1, one embodiment of the delivery system for high-energy pulsed laser light is illustrated in partial cross-section. The delivery system includes a catheter 10 comprising an outer tube 12 which houses the catheter components. The outer tube 12 has an outside diameter in the range of 1.3–3.0 mm, and is made from a suitably flexible plastic material that presents a low frictional resistance to its advancement along the interior of a patient's vascular system, such as polyurethane, for example. The catheter and tube are divided into two main sections. A distal section 14 is the portion of the catheter that is inserted into the patient's blood vessels. A proximal section 16 remains outside of the patient's body and connects to a pulsed laser source. These two sections are connected by a Y-adapter 18. The adapter 18 includes a first connector 20 which connects the proximal section 16 of the catheter to the distal section 14. A second connector 22 on the adapter provides for communication with a central lumen 24 in the distal section 12. As better shown in FIGS. 2–5, this central lumen is formed by an inner tube 26 that is concentric with the outer tube 12 of the catheter. The lumen 24 accommodates a guidewire 28 that extends through the distal section 14 of the catheter (FIG. 1).

A second lumen is formed in the catheter, in the annular space between the inner tube 26 and the outer tube 12. Disposed within this outer lumen of the catheter is a plurality of optical fibers 30. These fibers extend from the proximal end of the catheter to its distal end. A fiber that is particularly suitable for use in the delivery of high-energy pulsed ultraviolet laser light is a multi-mode fiber which has a relatively large core, or active area, relative to the area of its cladding, i.e., the outer skin of the fiber. The core is made of substantially pure synthetic fused silica, i.e., amorphous silicon dioxide. The term "substantially pure" means that the material preferably has a metallic impurity content of no more than 30 parts per million, to provide better conduction of the transmitted laser energy than that which is obtainable with natural fused quartz. The term "metallic impurity" includes both metals per se and oxides thereof.

Even with such a low level of metallic impurity, defects in the silica fiber can serve as linear and non-linear absorption sites for the photons. These defects can vary from oxygen vacancy to unbonded silicon atoms found in any silica glass. They can result in lowered transmittance of ultraviolet radiation. Increasing the intensity (or energy) of the laser light that is introduced into one end of a fiber exhibiting such defects will not necessarily result in proportionally increased output at the other end. Rather, the increased intensity level can reduce the threshold level at which bulk damage occurs to the silica glass, and thereby destroys the delivery system.

In accordance with one aspect of the present invention, the transmittance of high-energy UV laser light in a fiber made of synthetic silica is enhanced by lightly doping the silica with a material which functions to repair some of the inherent structural defects of the silica. The silica is preferably doped with an OH⁻ radical, to thereby form so-called "wet" silica. It is believed that defects in silica that affect UV light transmission comprise oxygen hole centers and unbonded silica atoms. It is theorized that the doping of the silica with the OH⁻ radical functions to repair these defects by eliminating the oxygen holes or vacancies in one case and by bonding to the silicon to form the $SiO_2$ double bond. It has been reported that pure silica having only about 5 parts per million (ppM) of an OH radical has an absorption coefficient which is 2–3 times greater than silica having about 1200 ppM of the radical. See J. H. Stathes et al, *Physical Review B.*, Vol. 29, 12, 1984, pp. 70–79. Other investigations have reported that an optical absorption band appears in silica fibers having a low OH⁻ content as a result of the fiber drawing process. See Kaiser et al, *J. Opt. Soc. Am.* 63, 1973, p. 1141 and *J. Opt. Soc. Am.* 63, 1974, p. 1765. Apparently, an increase in the OH⁻ content of silica reduces both types of absorption sites described above, and in accordance with the present invention this concept is applied to a system for delivering high peak energy ultraviolet laser pulses to thereby enhance the efficiency of the energy transmittance. Preferably, the substantially pure silica that makes up the fibers contains about 200 to 2000 ppM of the OH⁻ radical, most preferably 1200 ppM.

In another embodiment of the invention, the silica that is used to produce the fibers of the delivery system is doped with fluorine. Fluorine doped silica exhibits even lower attenuation than high OH silica. It appears that the fluorine functions to shift the absorption band gap in the $SiO_2$ structure, to facilitate the transmittance of a large number of photons at low wavelengths. For multimode fibers having diameters in the range of 100 micrometers to 1500 micrometers, the silica preferably should contain between 0.25 and 2.0 wt % fluorine, most preferably 1.0 wt %.

As a further feature of the invention, the silica can be doped with both the OH⁻ radical and fluorine. When both of these materials are used in combination, the OH⁻ radical content should range between 200 and 2000 ppM, and the fluorine should comprise between 0.5 and 3.0 wt % of the silica.

In the context of the present invention, the waveguide can be a single optical fiber or a bundle of fibers each having a diameter up to 200 microns. A bundle of close-packed small-diameter fibers is preferred because they provide greater overall flexibility and thereby more easily accommodate the twists and tight turns that are required to feed the delivery system through body cavities. This feature is particularly desirable where a larger diameter waveguide is required to deliver a relatively large diameter beam with uniform intensity, such as in vascular angioplasty.

A more detailed view of the distal tip of catheters employing multiple optical fibers is shown in FIGS. 2–5. FIGS. 2 and 3 relate to an embodiment having a large number of small diameter fibers. For example, each fiber can have a diameter in the range of 50–100 microns. In such an embodiment, a large number of fibers can be used, e.g. 100–225 fibers, to provide an effective ablation area. When a large number of such fibers are used, they are closely packed in the annular lumen formed between the inner tube 26 and the outer tube 12, as shown in FIG. 2.

Preferably, the fibers are free to move relative to one another within the annular lumen, to facilitate bending of the catheter. At the distal tip of the catheter, however, the fibers are fixed in place. Referring to FIG. 3, this fixing is accomplished by potting the tips of the fibers 30 with an adhesive 32, preferably an epoxy. After the potting, the distal ends of the fibers are polished to provide a smooth distal face. Also, the epoxy is used to form a rounded tip 34 at the end of the outer tube 12. This tip serves to protect the ends of the fibers and its rounded edges minimize trauma to the walls of the blood vessel as the catheter is being advanced. Both the fibers 30 and the inner tube 26 extend slightly beyond the outer tube, to the end of the catheter defined by the tip 34.

If desired, a marker 36 that is made from a radiopaque material, e.g. gold, can be incorporated into the tip structure. In one embodiment, the radiopaque marker forms a ring around the distal end of the fibers 30, and enables the physician to locate the distal tip of the catheter by means of an x-ray or the like.

Figure 5:
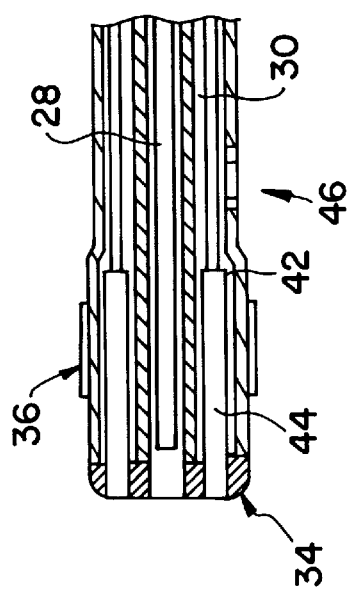
FIG. 5 is an enlarged cross-sectional side view of the distal end of another embodiment of a catheter having expanded distal tips.
Figure 7:
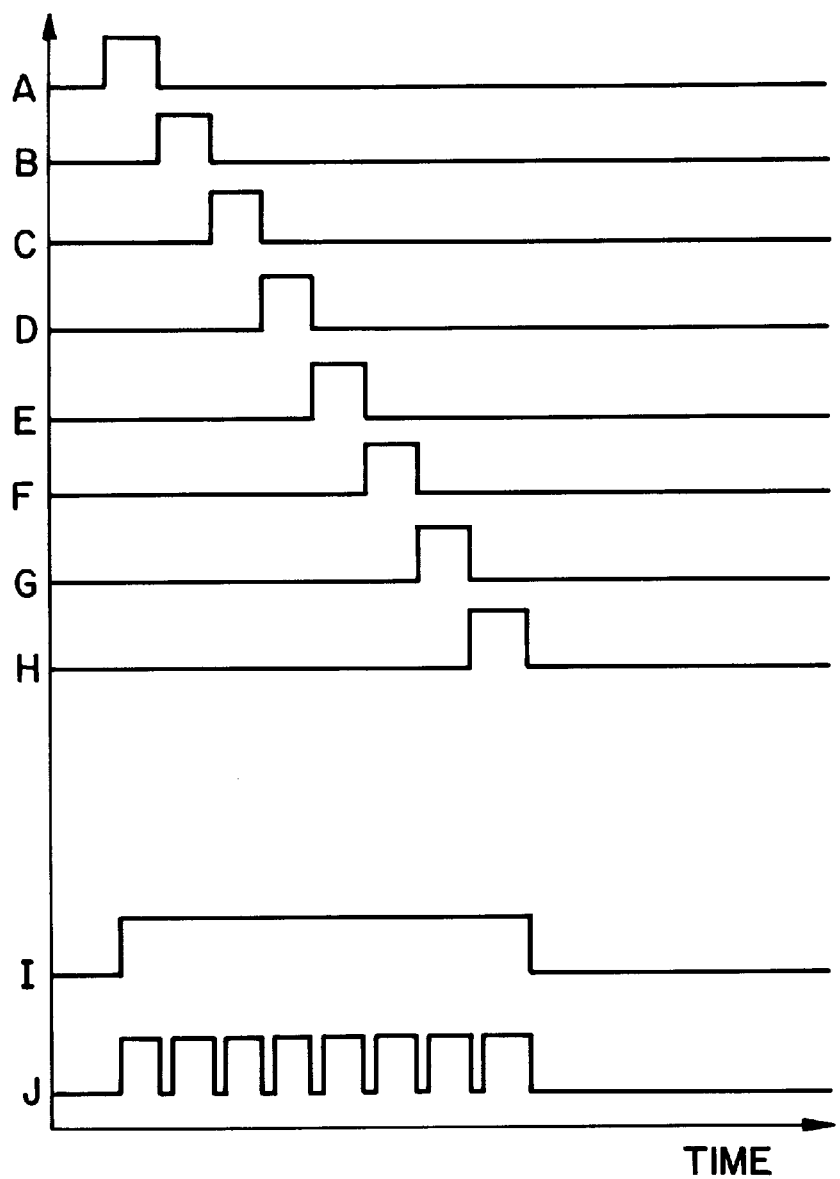
FIG. 7 is a graph showing pulse construction.

FIGS. 4 and 5 illustrate another embodiment of the catheter which uses a lesser number of fibers. More particularly, this embodiment employs twelve fibers 30, where the diameter of the distal end of each fiber can be up to 200 microns to provide the same ablation area. As can be seen, the fibers are arranged in a concentric ring around the inner tube 26.

While it is possible to employ 200 micron diameter fibers throughout the length of the catheter to transmit the laser energy, such a construction is not preferred because fibers of this diameter possess an appreciable amount of inherent stiffness, thereby making the guiding of the catheter more difficult. It is more desirable to use smaller diameter fibers, and to expand the diameter of the laser beam as it exits the distal end of the catheter. By expanding the diameter of the laser beam, for example by means of an increasing taper or fusing a larger diameter fiber at the distal end of the fiber, a larger area of tissue is ablated to produce more favorable results towards obtaining better blood flow in a blood vessel while using a small diameter flexible fiber that can be easily propagated through the vessel.

FIG. 5 illustrates an embodiment of a catheter having such beam-expanding structure. Here, each laser energy conducting fiber 30 is fused at its end face 42 to a short section of a larger diameter fiber 44. For example, a 100-micron diameter fiber 30 may have a short 200-micron diameter fiber 44 fused to its end. Each end fiber 44 can be about 3 mm long, and can be made from the same silica material as the fibers 30. By virtue of the larger diameter fiber at the distal end, the laser beam can expand as it emerges from the fiber 30, thereby providing a larger area of coverage and subsequently a larger ablation area. Furthermore, the plural fibers located symmetrically around the guidewire 28 provide uniform energy distribution over a larger area. Again, a radiopaque marker 36 can be provided around the distal tip of the catheter.

Except at the very end of the catheter where the epoxy 34 is present, there is free space within the outer annular lumen, between the fiber 30 and the walls of the lumen. If desired, this free space can be used to provide a saline solution, or other laser-transmitting media, to the site of the obstruction. The solution can be injected into the catheter through a suitable port at the proximal end, and emerge through holes 46 in the side wall of the catheter at its distal end.

As noted previously, every fiber comprises a core and a cladding which surrounds the core to maintain the transmitted light energy within the core. The cross-sectional area of the fiber might normally have a core/cladding ratio of 80/20 to provide suitable flexibility. Typically, both the core and the cladding are made of glass, with the cladding being appropriately modified (e.g., doped) to provide it with a lower index of refraction.

In accordance with one aspect of the invention, the conventional glass cladding is eliminated and the core of the fiber is directly surrounded by a coating of organic material. One specific preferred material is UV-cured acrylate. It has a lower index of refraction than silica, and thereby functions to maintain the laser energy within the core. It also serves to protect the silica glass, and hence eliminates the need for a discrete protective layer. This reduces the overall size of the fiber and hence enables the net cross-sectional area of the core to be increased for a delivery system having a given outer diameter.

Further details regarding the composition of preferred coatings can be found in U.S. Pat. No. 4,511,209, the disclosure of which is incorporated herein by reference.

At the proximal end of the catheter, pulsed energy from a laser 48 is coupled into the fibers by means of a coupler 50. The structure of the coupler is shown in greater detail in FIG. 6. As shown therein, the proximal ends of the fibers 30 terminate at a planar face 52. The ends of the fibers are held in place within a chamber 54, for example by means of a sleeve 56 to which they are bonded. In the illustrated embodiment, a plano-convex lens 58 converges the beam of light 60 from the laser 48 to a diameter which is slightly larger than that of the bundle of fibers. If desired, a port 62 can be used to connect the chamber to a vacuum source or to fill it with a dielectric liquid. The vacuum can be used to remove gases which could break down upon exposure to the concentrated laser beam and thereby adversely affect its coupling into the fibers. Alternatively, the dielectric liquid can have an index of refraction which is matched to that of the fibers 30, to reduce dielectric stress.

It is important to ensure that the surface 52 of the fibers is relatively free of gross scratches and other imperfections when air or a vacuum is present in the chamber 54. This can be accomplished by fire polishing or by heating the end of the fiber with a micro-torch to cause the fiber material to melt and flow slightly, to thereby remove the imperfections caused by manual polishing. Alternatively, the surface can be prepared by exposing the surface to high-energy ultraviolet laser pulses which cause a slight reflow of the silica material and vaporizes polishing impurities. For example, about 2000 pulses of energy having a density of 50 mJ/mm$^2$ produce a suitable finish.

To further increase the peak energy that is delivered through the system, it is preferable to increase the length of the pulses beyond the relatively short duration that is typically produced by commercial Excimer lasers and the like. For example, a pulse having a duration in the range of 10–3000 nsec, more preferably 100–300 nsec, enables much higher peak energy to be applied with the same delivery system than a conventional 10 nsec pulse, yet is still sufficiently short to produce the desired cutting action. One example of a circuit for stretching the output pulses of a laser is the magnetic switch developed at the Jet Propulsion Laboratory by Drs. J. Laudenslager and T. Pacala. The lengthening of the pulse duration reduces the peak power density at the input ends of the fibers while maintaining a high energy level to produce efficient ablation of tissue. More particularly, the fibers are more easily damaged by high power density than by high energy density. Power density (P) and energy (E) are related as follows:

$$P = \frac{E}{A \cdot t}$$

where A is the cross-sectional area of the laser beam, i.e. the diameter of the fiber bundle, and t is the length of the pulse. Thus, by increasing the length of the pulse, the power density is reduced while the energy density remains constant.

In this regard, it is not necessary that each lengthened or stretched pulse comprise a single, continuous pulse having a duration of 100–300 nsec, for example. Rather, it could comprise a burst of shorter length successive pulses which together provide an effective pulse length of the desired duration.

FIG. 6 depicts a pulse that is made up of a train or a group of temporally shifted subpulses. A high-energy long pulse I or J results from a super-positioning of numerous subpulses A-H produced by the laser, and has a shorter diffusivity of tissue. If the subpulses A-H overlap one another as shown in FIG. 6, a continuous lengthened pulse I will be produced. However, it is not necessary that the subpulses overlap. They can be slightly spaced to produce a pulse burst J within an envelope of 100–300 nsec duration. U.S. Pat. No. 4,677,636 relates to such laser pulses, and the subject matter thereof is incorporated herein by reference.

By stretching the duration of the pulses in this manner, a higher total amount of energy can be delivered to successfully ablate the tissue while keeping its instantaneous power density at a level which will not destroy the optical fibers. For example, the laser energy that is coupled into the proximal end 42 of the fibers can have an energy density of 50 mJ/mm$^2$ or more.

To use the catheter system, the guidewire 28 is threaded through the lumen of the blood vessel by means of an introducer catheter (not shown). The guidewire 28 is inserted up to the location of a total obstruction in the vessel, or in the case of a subtotal lesion, beyond the lesion.

The catheter 10 is then mounted onto the guidewire 28, with the guidewire extending through the inner lumen 24. The catheter 10 and the optical fibers 30, which are bound thereto, are then advanced along the guidewire 28 until the catheter 10 and the distal tips of the optical fibers 30 are adjacent the lesion to be ablated. Preferably, the distal tips of the fibers are in contact with the lesion. The combination of the guidewire 28 and the catheter 10 ensures that the optical fibers 30 remain in alignment with the blood vessel, thus avoiding perforation of the blood vessel by the tip of the optical fibers 30 during positioning of the fiber or by the laser beam during ablation.

Once the fibers 30 are adjacent the lesion, ablation of the lesion is conducted by transmitting laser pulses from the source 38 through the fibers. As the ablation occurs, the catheter 10 is advanced so that the tips of the fibers remain in contact with the lesion. During this process the guidewire acts as a track so that the catheter and the fibers remain aligned with the walls of the blood vessel, thereby avoiding perforation. Once the lasing is completed, the catheter 10 can be withdrawn, leaving the guidewire 28 in place within the blood vessel. Angiographic dye can then be injected through a guiding catheter around the guidewire 28 to evaluate the results of the lasing operation. If the results are unsatisfactory, the entire procedure can be repeated, possibly using different laser parameters or fibers, or other types of coronary catheters.

The Excimer energy emerging from the fibers 30 is only capable of ablating a lesion in a forward direction. If the fibers are not in contact with the lesion, the blood between the lesion and the optical fibers should be displaced with a solution that is transparent to the laser, such as saline. However, when the fibers contact the lesion, the laser transmitted through the optical fibers is capable of ablating a lesion in a blood field. In either case, there is no necessity to block the blood flow around the catheter during the ablation process.

Figure 8:
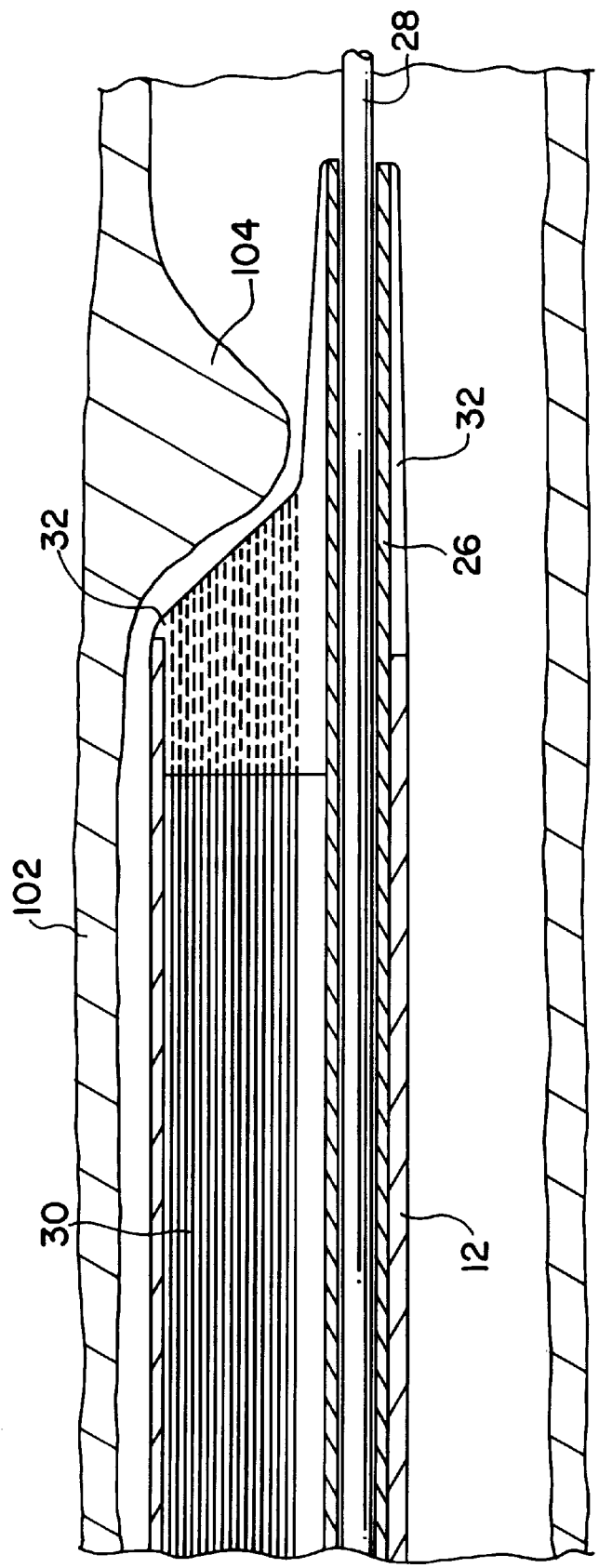
FIG. 8 is a perspective view of a multilumen eccentric catheter.

In an alternate embodiment of the catheter, the guidewire 28 is eccentrically positioned within the catheter. Referring to FIG. 8, the inner tube 26 which defines the guidewire lumen is disposed adjacent one side of the outer tube 12, and the optical fibers 30 are disposed in the remaining space between the other side of the outer tube 12 and the inner tube 26. The inner tube 26 extends beyond the outer tube 12, and the epoxy 32 defines a continuous contour between the ends of these two tubes. The optical fibers 30 extend to the edge of the contoured shape.

In use, the guidewire 28 is first passed through the blood vessel 102 to a point beyond the lesion 104. The catheter is then advanced over the guidewire until the distal ends of the fibers come in contact with the lesion, at which point the laser energy is transmitted to the site to be ablated. During ablation, the catheter can be rotated around the guidewire, to produce a larger ablation area.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. An angioplasty system, comprising:
   an elongated catheter that is adapted to fit within a human blood vessel, said catheter having a proximal end, a distal end and a longitudinal lumen that is open to said distal end for receiving a guidewire;
   a plurality of fiber-optic waveguides in said catheter each having an energy-conducting core made of synthetic silica that is substantially free of metallic impurities, and extending to said distal end for emitting energy conducted therethrough in a direction generally forwardly of said distal end of said catheter; and
   a pulsed XeCl Excimer laser having an output wavelength of about 308 nm, with each pulse having a duration between 100 nsec and 3000 nsec and being coupled into a proximal end of said fiber-optic waveguides at a density of at least 50 mJ/mm$^2$ to ablate atherosclerotic plaque in a blood vessel.

2. The angioplasty system of claim 1 wherein each of said fiber-optic waveguides has a diameter no greater than about 200 microns.

3. The angioplasty system of claim 1 wherein the energy-conducting core of each waveguide is surrounded by cladding that is made of glass material.

4. The angioplasty system of claim 1 wherein the core of each of said waveguides is doped with fluorine.

5. The angioplasty system of claim 1 wherein each pulse of said laser energy comprises a sequence of time shifted subpulses.

6. The angioplasty system of claim 1 wherein the core of each of said waveguides is doped with an OH$^-$ radical.

7. The angioplasty system of claim 6 wherein said OH$^-$ radical is present in the core at a concentration of 200–2000 parts per million.

8. An angioplasty system, comprising:
   an elongated catheter that is adapted to fit within a human blood vessel, said catheter having a proximal end, a distal end and a longitudinal lumen that is open to said distal end for receiving a guidewire;
   a plurality of fiber-optic waveguides disposed around said guidewire lumen in said catheter, and each having an energy-conducting core made of synthetic silica that is substantially free of metallic impurities, a glass material cladding surrounding said core, and a diameter no greater than about 200 microns, and extending to said distal end for emitting energy conducted therethrough in a direction generally forwardly of said distal end of said catheter; and
   a pulsed XeCl Excimer laser having an output wavelength of about 308 nm, with each pulse having a duration between 100 nsec and 3000 nsec, and being coupled into a proximal end of said fiber-optic waveguides at a density of at least 50 mJ/mm$^2$ to ablate atherosclerotic plaque in a blood vessel.

9. The angioplasty system of claim 8 wherein said fiber optic waveguides are disposed substantially symmetrically about said guidewire lumen.

* * * * *